United States Patent [19]

Saiki et al.

[11] Patent Number: 5,639,657

[45] Date of Patent: Jun. 17, 1997

[54] PROCESS FOR FORMATION OF ARTIFICIAL SEAWEED BED

[75] Inventors: Masamichi Saiki; Sadao Ueda; Shuji Kitao, all of Kanagawa, Japan

[73] Assignees: Nippon Tetrapod Co., Ltd.; Toyo Glass Co., Ltd., both of Tokyo, Japan

[21] Appl. No.: 217,629

[22] Filed: Mar. 24, 1994

[30] Foreign Application Priority Data

Mar. 30, 1993 [JP] Japan .................................. 5-093894

[51] Int. Cl.⁶ .............................. C12N 5/00; C12N 11/14; A01K 61/00; E02B 3/04
[52] U.S. Cl. ........................ 435/410; 119/221; 405/24; 435/174; 435/176; 435/420; 47/59
[58] Field of Search .................................. 435/174, 176, 435/240.45, 240.4; 405/23, 24, 32; 119/221

[56] References Cited

U.S. PATENT DOCUMENTS

| | | | |
|---|---|---|---|
| 4,465,399 | 8/1984 | Kikazawa et al. ........................ | 405/32 |
| 4,898,712 | 2/1990 | Dosaj et al. ........................... | 420/578 |
| 4,913,734 | 4/1990 | Romenets et al. ...................... | 75/501 |

*Primary Examiner*—David M. Naff
*Attorney, Agent, or Firm*—McAulay Fisher Nissen Goldberg & Kiel, LLP

[57] ABSTRACT

A process for the formation of an artificial seaweed bed comprises depositing a structure as an artificial fish reef in the sea. According to the present invention, the structure is made of a glassy material having a specific composition, or a surface of the structure is covered with the specific glassy material. The glassy material contains silicon in an amount of 30 to 70 wt. % in terms of $SiO_2$. The glassy material further contains sodium and/or potassium in an amount of 10 to 50 wt. % in terms of $Na_2O$ and/or $K_2O$. The glassy material furthermore contains iron in an amount of 5 to 50 wt. % in terms of $Fe_2O_3$. All or a part of the iron is present in a ferrous state. The glassy material contains the ferrous iron in an amount of not less than 1 wt. %.

15 Claims, 1 Drawing Sheet

PROCESS FOR FORMATION OF ARTIFICIAL SEAWEED BED

FIELD OF THE INVENTION

The present invention relates to a process for the formation of an artificial seaweed bed (marine macrophyte bed), which is a habitat of a seaweed (marine macrophyte) or a plant plankton. The seaweed bed provides a nursery ground for fishes.

BACKGROUND OF THE INVENTION

A structure is deposited as an artificial fish reef in the sea to form an artificial seaweed bed. The structure is made of steel, stone or wood. The artificial seaweed bed is formed in a space formed of the structure. The space provides a habitat for a seaweed or a plant plankton. The process for the formation of the artificial seaweed is widely applicable.

The conventional seaweed bed attracts grown fishes. Accordingly, the seaweed bed provides an artificial fishing ground. However, the amount of the seaweed planted on the artificial bed has remarkably been decreased within several years from the time of depositing the artificial fish reef. Therefore, the conventional artificial seaweed bed cannot provide a nursery ground for a fish. In other words, the seaweed bed cannot protect fish eggs and young fishes of a plankton life type. A seaweed or a plant plankton should be planted on an artificial fish reef for a long term to provide a nursery ground for fishes. It is now required to develop such an artificial seaweed bed and an artificial fish reef.

By the way, Katsuhiko Matsunaga (Hokkaido University) describes that minerals dissolved in seawater such as iron, manganese, silicon and phosphorus are necessary for cultivating a seaweed or a plant plankton on a seaweed bed (Dairy Politics and Economics News, Jan. 1, 1988). He further reports that the cultivating effect can be remarkably increased by dissolving a ferrous ion (divalent iron ion) in seawater.

Further, it has been experimentally known that a sunken ship is thickly grown with seaweed, which attracts many fishes. The ship in the sea forms an artificial fish reef made of iron. It is assumed that a part of iron of the ship is dissolved in seawater as a ferrous ion, which can be directly furnished to the organisms on the seaweed bed. The assumption is supported by data about iron contents in seaweed. The iron content in a seaweed planted on the artificial iron reef is twice or more the content in a seaweed planted on a natural rock reef.

SUMMARY OF THE INVENTION

If minerals, particularly ferrous iron and additionally manganese, silicone, phosphorus were incorporated into a structure for an artificial fish reef, the organisms could be cultivated on a seaweed bed more effectively. However, it is technically difficult to incorporate such minerals into conventional structures made of steel, stone or wood. Further, the minerals contained in the structure should be stably and continuously dissolved in seawater for a long term. It is also difficult to arrange the minerals contained in the structure to be dissolved in such a manner.

An object of the present invention is to provide an artificial seaweed bed which stably and continuously furnishes minerals to a seaweed or a plant plankton.

The present invention provides a process for the formation of an artificial seaweed bed which comprises depositing a structure as an artificial fish reef in the sea, wherein the structure is made of a glassy material which contains silicon in an amount of 30 to 70 wt. % in terms of $SiO_2$, sodium and/or potassium in an amount of 10 to 50 wt. % in terms of $Na_2O$ and/or $K_2O$, and iron in an amount of 5 to 50 wt. % in terms of $Fe_2O_3$, all or a part of said iron being present in a ferrous state, and said glassy material containing the ferrous iron in an amount of not less than 3 wt. %.

The invention also provides a process for the formation of an artificial seaweed bed which comprises depositing a structure as an artificial fish reef in the sea, wherein a surface of the structure is covered with a glassy material which contains silicon in an amount of 30 to 70 wt. % in terms of $SiO_2$, sodium and/or potassium in an amount of 10 to 50 wt. % in terms of $Na_2O$, and/or $K_2O$, and iron in an amount of 5 to 50 wt. % in terms of $Fe_2O_3$, all or a part of said iron being present in a ferrous state, and said glassy material containing the ferrous iron in an amount of not less than 3 wt. %.

The present inventors note that the minerals contained in the above-mentioned glassy material are stably and continuously dissolved in seawater. Accordingly, the artificial fish reef of the present invention can furnish minerals such as iron (particularly ferrous iron) and silicon (optionally phosphorus, manganese or the like) to a seaweed or a plant plankton. The artificial seaweed bed formed according to the present invention can be effective for a long term. Therefore, the artificial seaweed bed not only attracts the grown fishes, but also provides a nursery ground for the attracted fishes.

The glassy material can be made from waste glass such as waste bottle or glass board by adjusting the ingredients contained in the waste glass. Accordingly, the present invention is advantageous in view of the utilization of waste material.

The present invention has another advantage that it is easy to adjust the contents of the minerals to be dissolved in seawater.

DETAILED DESCRIPTION OF THE INVENTION

Figure 1:
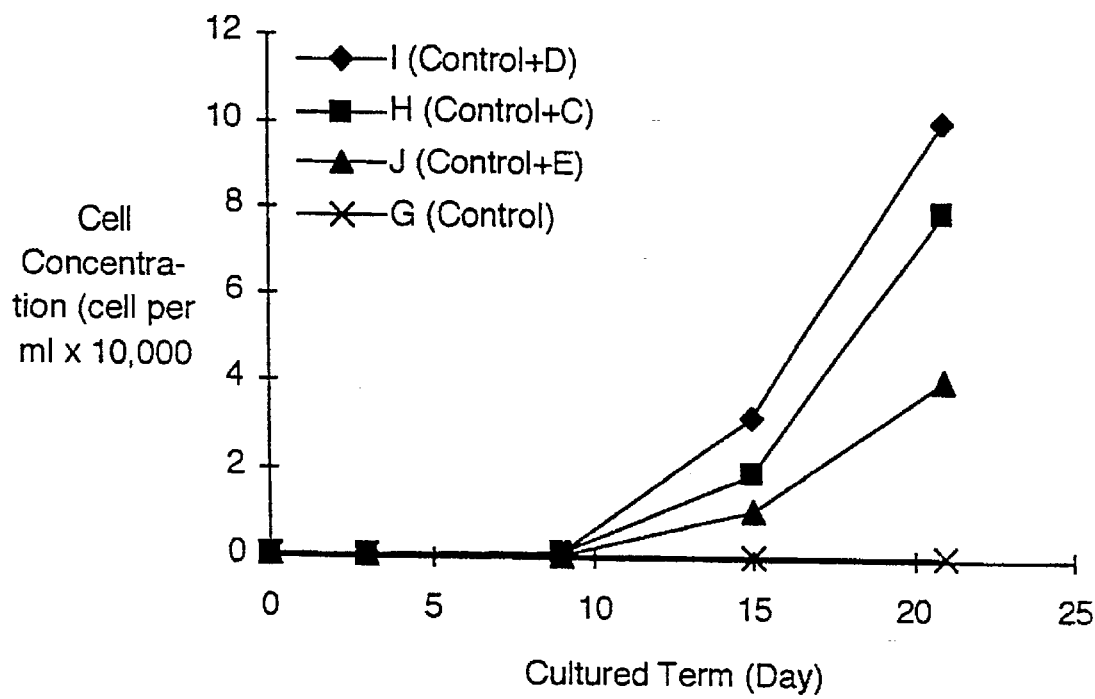
FIG. 1 is a graph showing the results of a comparative experiment about growth of diatom. Cultures containing the glassy material of the present invention are compared with a control culture.

The present invention is characterized in that the surface of the structure as an artificial fish reef is covered with a specific glassy material.

The glassy material contains silicon in an amount of 30 to 70 wt. % (preferably 35 to 60 wt. %) in terms of $SiO_2$. The glassy material further contains sodium and/or potassium in an amount of 10 to 50 wt. % (preferably 20 to 30 wt. %) in terms of $Na_2O$ and/or $K_2O$. The glassy material furthermore contains iron in an amount of 5 to 50 wt. % (preferably 10 to 35 wt. %) in terms of $Fe_2O_3$. All or a part of the iron is present in a ferrous state. The glassy material contains the ferrous iron in an amount of not less than 1 wt. % (preferably not less than 3 wt. %, more preferably not less than 5 wt. %, and most preferably not less than 8 wt. %, and preferably not more than 30 wt. %). In the present specification, the unit "wt. %" is calculated based on the total amount of the glassy material. Further, the expression "in terms of" means that the amount of an element such as silicon is converted into the amount of a standard compound such as $SiO_2$.

The present inventors have noted the character of the vitreous structure of the glassy material, which is different from the structures of metal or concrete materials. In the present invention, the glassy material is used as a matrix, and iron including ferrous iron is trapped in the matrix. The present inventors have discovered that the trapped iron stably and slowly releases iron ions including ferrous ions to seawater for a long term. The present invention is made by the discovery of the inventors.

The glassy material preferably contains phosphorus in an amount of 1 to 30 wt. % in terms of $P_2O_5$. Further, the glassy material preferably contains manganese in an amount of 0.1 to 5 wt. % in terms of MnO.

Silicon and oxygen atoms contained in the glassy material form a network structure of the matrix. Sodium and potassium atoms are modifiers of the network structure, which are incorporated into the structure. Iron atom can form the network structure or function as a modifier. When the glassy material of the above-mentioned structure is immersed in seawater, water molecules gradually and slowly cut the network. Accordingly, the components of the glassy material are gradually dissolved in water for a long term. Accordingly, the glassy material is slowly soluble in water.

Further, phosphorus atom forms the network structure. Manganese atom can form the network structure or function as a modifier. In the case that phosphorus or manganese is further contained in the glassy material, the material can gradually release phosphorus or manganese for a long term as the network of them is slowly cut or broken with water. As is mentioned above, the components to be dissolved and the dissolving rates of the components can be arranged by adjusting the composition of the glassy material and the amounts of the components.

The glassy material can be prepared according to a known glass manufacturing method, which comprises heating the known materials containing silicon, iron, sodium and/or potassium at a high temperature (for example, at 1,300° to 1,500° C. for about 10 minutes or more) to melt them, and cooling them. The melting step in the glass manufacturing method can be conducted under reducing atmosphere to increase the content of ferrous iron contained in the glassy material. The reducing atmosphere can be arranged by using a reducing agent such as coke or a reducing gas such as carbon monoxide. In the case that optional components such as manganese or phosphorus are incorporated into the glassy material, the materials containing the components can be mixed with the above-mentioned materials, before melting the mixture at a high temperature.

The glassy material used in the present invention can have a porous surface. The contact area between glass and seawater can be increased by covering the surface of an artificial fish reef with the porous glass. Accordingly, the porous structure of the glass accelerates dissolving the elemental components of the glass in seawater.

The glassy material can be made from used waste glass. For example, the glassy material used in the present invention can be prepared by crashing used bottle, adding some materials containing necessary elemental components to the waste glass, and melting the mixture under reducing atmosphere, as is mentioned above.

The glassy material can be coated on a surface of another structure to form an artificial fish reef. The structure can be made of various substances such as concrete, steel, natural rock or a waste product. The glassy material can be mixed with another substance before coating them on the structure.

The artificial fish reef is deposited in the sea to form an artificial seaweed bed. In seawater around the seaweed bed, minerals such as silicon and ferrous iron are stably released from the surface of the artificial fish reef, which is made of a glassy material containing silica, iron, sodium and/or potassium, and particularly containing an increased amount of ferrous iron. The artificial seaweed bed not only attracts fishes, but also provides a nursery ground for the attracted fishes by cultivating a seaweed or a plant plankton for a long term. Accordingly, the artificial seaweed is also effective for cultivating the fished. The artificial seaweed bed formed according to the present invention can be used for a long term.

EXAMPLE 1

Compositions for a glassy material comprising 10 weight parts of hematite powder, 50 weight parts of siliceous sand, 50 weight parts of potassium phosphate, 15 weight parts of phosphoric acid, 2 weight parts of manganese dioxide and 2 weight parts of coke were well mixed and placed in a crucible. The crucible was placed in a furnace preheated to 1,400° C. The mixture was heated for 1 hour under reducing atmosphere using coal gas. The mixture was then cooled to room temperature to obtain a glassy material A according to the present invention.

Compositions for a glassy material comprising 30 weight parts of hematite powder, 50 weight parts of siliceous sand, 25 weight parts of sodium carbonate, 25 weight parts of potassium phosphate, 2 weight parts of manganese dioxide and 5 weight parts of coke were well mixed and placed in a crucible. The crucible was placed in a furnace preheated to 1,400° C. The mixture was heated for 1 hour under reducing atmosphere using coal gas. The mixture was then cooled to room temperature to obtain a glassy material B according to the present invention.

EXAMPLE 2

Compositions for a glassy material comprising 30 weight parts of hematite powder, 50 weight parts of siliceous sand, 25 weight parts of soda ash, 50 weight parts of potassium phosphate and 5 weight parts of coke were well mixed and placed in a crucible. The crucible was placed in a furnace preheated to 1,400° C. The mixture was heated for 1 hour under reducing atmosphere using coal gas. The mixture was then cooled to room temperature to obtain a glassy material C according to the present invention.

Compositions for a glassy material comprising 9 weight parts of hematite powder, 50 weight parts of siliceous sand, 20 weight parts of soda ash, 18 weight parts of potassium phosphate and 4 weight parts of coke were well mixed and placed in a crucible. The crucible was placed in a furnace preheated to 1,400° C. The mixture was heated for 1 hour under reducing atmosphere using coal gas. The mixture was then cooled to room temperature to obtain a glassy material D according to the present invention.

Compositions for a glassy material comprising 20 weight parts of hematite powder, 50 weight parts of siliceous sand, 37.3 weight parts of soda ash, 44.1 weight parts of potassium carbonate and 1 weight part of coke were well mixed and placed in a crucible. The crucible was placed in a furnace preheated to 1,400° C. The mixture was heated for 1 hour under reducing atmosphere using coal gas. The mixture was then cooled to room temperature to obtain a glassy material E according to the present invention.

Evaluation of Glassy Materials

The glassy materials A, B, C, D and E obtained in Examples 1 & 2 were subjected to an elemental analysis. The results are set forth in Table 1. In Table 1, the amounts of the elements are converted into the amounts of oxides.

TABLE 1

| Sample No. | Composition of glassy material (wt. %) | | | | | | |
|---|---|---|---|---|---|---|---|
| | $Fe_2O_3$ | $SiO_2$ | $Na_2O$ | $K_2O$ | $P_2O_5$ | MnO | $Al_2O_3$ |
| A | 8.8 | 44.8 | — | 23.7 | 21.6 | 1.1 | 0.04 |
| B | 27.2 | 46.4 | 13.5 | 7.4 | 3.7 | 1.1 | 0.04 |
| C | 27.7 | 47.2 | 13.8 | 7.5 | 3.8 | — | 0.04 |
| D | 10.4 | 58.9 | 13.8 | 11.3 | 5.7 | — | 0.04 |
| E | 15.1 | 38.6 | — | 38.5 | 7.7 | — | 0.03 |

Further, the amounts of ferrous iron ($Fe^{2+}$) contained in the glassy materials A, B, C, D and E were measured according to Mössbauer spectral method. The results are shown below.

| | | Contents of $Fe^{2+}$ | | |
|---|---|---|---|---|
| A | B | C | D | E |
| 4.9 wt. % | 15.2 wt. % | 15.5 wt. % | 5.8 wt. % | 8.5 wt. % |

Next, elution tests for iron and silicon were conducted with respect to each of the glassy materials A, B, C, D and E in the following manner.

The glassy material was crashed in an agete mortar. The crashed sample was screened through a sieve of No. 18 (850 μm). The screened fraction was further screened through a sieve of No. 50 (300 μm). The screened extremely fine fraction was removed. The fraction remaining on the sieve of No. 50 was gently washed with the sieve in water for 1 minute. The fraction was further washed in ethanol, and dried at 100° C. for 30 minutes. The fraction was cooled in a desiccator to obtain a test sample. In an Erlenmeyer flask made of hard glass (volume: 200 ml), 10 g of the test sample was placed. In the flask, 100 ml of pure water was further placed. The flask was covered with a watch glass, and heated for 2 hours in water bath. After heating, the flask was immediately cooled in running water to obtain a solution eluted from the sample.

The above-mentioned elution test corresponds to the elution within about 7 months in water at room temperature.

The eluted amounts of iron (total amount), ferrous iron, manganese and silicon dioxide were measured with respect to the sample solutions in the following manner. Further, casting powder (chemical composition (wt. %), C: 3.6, Si: 2.0, Mn: 0.6, Ni: 1.0, Fe: 92.0, others: P, S, Cr) and slag of electric steel (chemical composition (wt. %), $Fe_2O_3$: 44.7, FeO: 14.4, $SiO_2$: 8.2, CaO: 11.0, MgO: 4.3, $Al_2O_3$: 6.8, $Cr_2O_3$: 2.1) were crashed and eluted in the same manner to obtain control sample solutions. The eluted amounts of the control solutions were measured in the same manner.

(1) Quantitative Analysis of Iron (Total Amount)

In a measuring flask of 100 ml, 25 ml of the sample solution (10 ml if the sample solution was colored) was placed. To the solution, 2 ml of 5% (weight per volume) solution of ascorbic acid was added. Further, 10 ml of 0.1% (weight per volume) aqueous solution of o-phenanthroline was added to the solution. Furthermore, 15 ml of 20% (weight per volume) aqueous solution of ammonium acetate was added to the solution. Water was added to a standard line of the flask. The solution was left for 30 minutes. A part of the solution was placed in a measuring cell. The light absorbance was measured at 510 nm. The amount of iron was calculated by the light absorbance of the sample and the absorbance of water (control).

(2) Quantitative Analysis of Ferrous Iron

In a measuring flask of 100 ml, 25 ml of the sample solution was placed. To the solution, 10 ml of 0.1% (weight per volume) aqueous solution of o-phenanthroline was added. Further, 15 ml of 20% (weight per volume) aqueous solution of ammonium acetate. Water was added to a standard line of the flask. The solution was left for 30 minutes. A part of the solution was placed in a measuring cell. The light absorbance was measured at 510 nm. The amount of ferrous iron was calculated by the light absorbance of the sample and the absorbance of water (control).

(3) Quantitative Analysis of Manganese

The manganese content was determined by measuring the light absorbance of the sample solution at 279.5 nm according to an atomic absorption analysis.

(4) Quantitative Analysis of Silicon Dioxide

In a plastic beaker of 25 ml, 25 ml of the sample solution was placed. Further, 2 ml of aqueous hydrofluoric acid solution (1 volume part of hydrofluoric acid and 9 volume parts of distilled water) was added to the solution. Furthermore, 2 ml of ammonium molybdate was added to the solution. The mixture was left for 10 minutes. Then, 5 ml of an aqueous tartaric acid solution was added to the solution. Further, 2 ml of 5% (weight per volume) aqueous solution of ascorbic acid. The resulting solution was placed in a measuring flask of 100 ml. Water was added to a standard line of the flask. The solution was left for 30 minutes. A part of the solution was placed in a measuring cell. The light absorbance was measured at 650 nm. The amount of silicon dioxide was calculated by the light absorbance of the sample and the absorbance of water (control).

The results are set forth in Table 2.

TABLE 2

| Sample No. | Eluted amount (μg per 10 g) | | | |
|---|---|---|---|---|
| | Total iron | $Fe^{2+}$ | Manganese | $SiO_2$ |
| A | 56,100 | 1,530 | 290 | 1,100 |
| B | 1,120 | 330 | 70 | 11,400 |
| C | 1,120 | 410 | — | 10,100 |
| D | 1,810 | 540 | — | 72,500 |
| E | 22,800 | 690 | — | 15,700 |
| Casting | 86 | 29 | — | — |
| Slag | 14 | 3 | — | — |

As is shown in the results of Table 2, the glassy materials of the present invention release sufficient amounts of minerals such as iron (particularly ferrous iron) and silicon dioxide for a long term, compared with the casting powder or the slag of electric steel. Accordingly, the glassy materials of the invention are effectively available for forming seaweed bed.

EXAMPLE 3

Compositions for a glassy material comprising 50 weight parts of hematite powder, 50 weight parts of crashed sodalime glass (crashed glass bottle) of several millimeters to several centimeters and 5 weight parts of coke were well mixed and placed in a crucible. The crucible was placed in a furnace, and heated from room temperature to 1,200° C. for 2 hours. The mixture was then cooled to room temperature to obtain a glassy material F according to the present invention.

Eluting tests about iron, ferrous iron and silicon dioxide were conducted with respect to the obtained glassy material F in the same manner as in Examples 2 and 3. The results are set forth in Table 3.

TABLE 3

| Sample No. | Eluted amount (μg per 10 g) | | |
|---|---|---|---|
| | Total iron | Ferrous iron | $SiO_2$ |
| F | 59 | 12 | 1,060 |

As is shown in the results of Table 3, the glassy material of the present invention releases sufficient amounts of minerals such as iron (particularly ferrous iron) and silicon dioxide for a long term, even though the material is not in the form of fine particles. Accordingly, the glassy material of the invention is effectively available for forming seaweed bed.

Evaluation of Glassy Material for Forming Seaweed Bed

A control culture ($NaNO_3$:75 mg, $NaH_2PO_4.2H_2O$:6 mg, $Na_2SiO_3.2H_2O$:10 mg, $CoSO_4.7H_2O$:12 μg, $ZnSO4.7H_2O$:21 μg, $MnCl_2.4H_2O$:180 μg, $CuSO_4.5H_2O$:7 μg, $Na_2MoO_4.2H_2O$:7 μg, seawater 1,000 ml) was prepared.

(1) Preparation of Sample Cultures

Sample culture G: The above prepared control culture was used.

Sample culture H: To 100 ml of the control culture, 10 mg of the glassy material C (graininess: 300 to 850 μm) was added.

Sample culture I: To 100 ml of the control culture, 10 mg of the glassy material D (graininess: 300 to 850 μm) was added.

Sample culture J: To 100 ml of the control culture, 10 mg of the glassy material D (graininess: 300 to 850 μm) was added.

(2) Culturing Test I of the Sample Cultures

Diatom (*Chaetocerros sociale*) was added to sample cultures in an amount of 300 cells (plankton cells) per ml. The temperature was kept at 5° C. The culture was exposed to light of 3,000 lux for the first 12 hours, and then was not exposed to light for the next 12 hours. This cycle was continued for 21 days. The density of the diatom cells was measured. The results are set forth in FIG. 1.

(3) Culturing Test II of the Sample Cultures

Flagellata (*Gymnodinium mikimotoi*) was added to sample cultures in an amount of 100 cells (plankton cells) per ml. The temperature was kept at 5° C. The culture was exposed to light of 3,000 lux for the first 12 hours, and then was not exposed to light for the next 12 hours. This cycle was continued for 22 days. The density of the flagellata cells was measured. The results are set forth in FIG. 2.

(4) Evaluation

Figure 2:
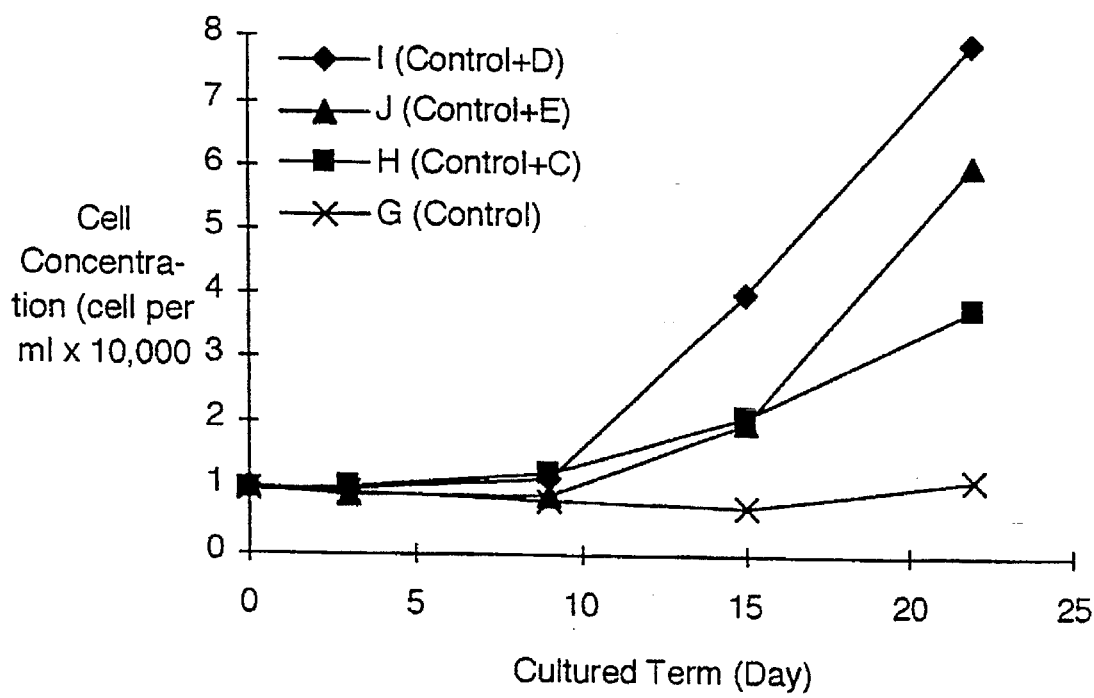
FIG. 2 is a graph showing the results of a comparative experiment about growth of flagellata. Cultures containing the glassy material of the present invention are compared with a control culture.

As is shown in FIGS. 1 and 2, the cell densities of diatom and flagellata were scarcely increased in the control culture G, even if the cells were cultured for 21 or 22 days. On the other hands, the diatom cells were increased about 130 to 300 times in the cultures H, I and J of the present invention after the cells were cultured for 21 days. Further, the flagellata cells were also increased about 3 to 8 times in the cultures H, I and J of the present invention after the cells were cultured for 22 days.

It is apparent from the above-mentioned results that the glassy materials of the invention effectively culture the plant plankton. Accordingly, the present invention forms an effective artificial seaweed bed for the plant plankton.

Moving Test of Iron From Glassy Material to Sea Tangle

In 1 liter of seawater, 10 mg of the glassy material C (graininess: 300 to 850 μm) was added. The mixture was divided to obtain four sample solutions. Sample sea tangles (kelps) K, L, M and N (immediately after gathered from the sea) of about 20 cm were placed In the sample solutions. The temperature was kept at 10° C. The culture was exposed to light of 3,000 lux for the first 12 hours, and then was not exposed to light for the next 12 hours. This cycle was continued for 10 days. The cultured sea tangles were dissolved in sulfuric acid. The iron contents of the obtained sea tangle solutions were measured in the same manner as is described above.

Before the above culturing experiments, the iron contents of the sea tangle solutions were measured with respect to the sample sea tangles K, L, M and N. The results are set forth in Table 4.

TABLE 4

| | Iron content in sea tangle (μg per g of dry wt.) | | | | |
|---|---|---|---|---|---|
| Culture | K | L | M | N | Average |
| Before | 7.3 | 8.9 | 9.4 | 8.8 | 8.6 |
| After | 16.5 | 15.5 | 16.3 | 17.4 | 16.4 |

As is shown in the results of Table 4, the iron contents of the sea tangles were increased about twice after culturing them according to the present invention. Accordingly, the iron contained in the glassy material of the present invention can be effectively incorporated into seaweed such as sea tangles. The incorporated iron accelerates the growth of the seaweed, as is reported by Katsuhiko Matsunaga (Dairy Politics and Economics News, Jan. 1, 1988). Accordingly, the present invention forms an effective artificial seaweed bed for the seaweed.

We claim:

1. A process for the formation of an artificial seaweed bed which comprises depositing a structure as an artificial fish reef in the sea, wherein the structure is made of a vitreous material which contains silicon in an amount of 30 to 70 wt. % in terms of $SiO_2$, sodium and/or potassium in an amount of 10 to 50 wt. % in terms of $Na_2O$ and/or $K_2O$, and iron in an amount of 5 to 50 wt. % in terms of $Fe_2O_3$, all or a part of said iron being present in a ferrous state, and said vitreous material containing the ferrous iron in an amount of not less than 1 wt. %.

2. The process for the formation of an artificial seaweed bed as claimed in claim 1, wherein the vitreous material contains the silicon in an amount of 35 to 60 wt. % in terms of $SiO_2$.

3. The process for the formation of an artificial seaweed bed as claimed in claim 1, wherein the vitreous material contains the sodium and/or potassium in an amount of 20 to 30 wt. % in terms of $Na_2O$ and/or $K_2O$.

4. The process for the formation of an artificial seaweed bed as claimed in claim 1, wherein the vitreous material contains the iron in an amount of 10 to 35 wt. % in terms of $Fe_2O_3$.

5. The process for the formation of an artificial seaweed bed as claimed in claim 1, wherein the vitreous material contains the ferrous iron in an amount of not less than 3 wt. %.

6. The process for the formation of an artificial seaweed bed as claimed in claim 1, wherein the vitreous material further contains phosphorus in an amount of 1 to 30 wt. % in terms of $P_2O_5$.

7. The process for the formation of an artificial seaweed bed as claimed in claim 1, wherein the vitreous material further contains manganese in an amount of 0.1 to 5 wt. % in terms of MnO.

8. A process for the formation of an artificial seaweed bed which comprises depositing a structure as an artificial fish reef in the sea, wherein a surface of the structure is covered with a vitreous material which contains silicon in an amount of 30 to 70 wt. % in terms of $SiO_2$, sodium and/or potassium in an amount of 10 to 50 wt. % in terms of $Na_2O$ and/or $K_2O$, and iron in an amount of 5 to 50 wt. % in terms of $Fe_2O_3$, all or a part of said iron being present in a ferrous state, and said vitreous material containing the ferrous iron in an amount of not less than 1 wt. %.

9. The process for the formation of an artificial seaweed bed as claimed in claim 8, wherein the vitreous material contains the silicon in an amount of 35 to 60 wt. % in terms of $SiO_2$.

10. The process for the formation of an artificial seaweed bed as claimed in claim 8, wherein the vitreous material contains the sodium and/or potassium in an amount of 20 to 30 wt. % in terms of $Na_2O$ and/or $K_2O$.

11. The process for the formation of an artificial seaweed bed as claimed in claim 8, wherein the vitreous material contains the iron in an amount of 10 to 35 wt. % in terms of $Fe_2O_3$.

12. The process for the formation of an artificial seaweed bed as claimed in claim 8, wherein the vitreous material contains the ferrous iron in an amount of not less than 3 wt. %.

13. The process for the formation of an artificial seaweed bed as claimed in claim 8, wherein the vitreous material further contains phosphorus in an amount of 1 to 30 wt. % in terms of $P_2O_5$.

14. The process for the formation of an artificial seaweed bed as claimed in claim 8, wherein the vitreous material further contains manganese in an amount of 0.1 to 5 wt. % in terms of MnO.

15. The process for the formation of an artificial seaweed bed as claimed in claim 8, wherein the structure is made of a material selected from the group consisting of concrete, steel, natural rock, and combinations thereof.

* * * * *